United States Patent
Shimoirisa (10) Patent No.: US 11,462,015 B2
(45) Date of Patent: Oct. 4, 2022

(54) INGREDIENT INQUIRY SYSTEM, INGREDIENT INQUIRY METHOD, AND INGREDIENT INQUIRY PROGRAM

(71) Applicant: TOSHIBA TEC KABUSHIKI KAISHA, Tokyo (JP)

(72) Inventor: Shinichi Shimoirisa, Shizuoka (JP)

(73) Assignee: TOSHIBA TEC KABUSHIKI KAISHA, Tokyo (JP)

( * ) Notice: Subject to any disclaimer, the term of this patent is extended or adjusted under 35 U.S.C. 154(b) by 52 days.

(21) Appl. No.: 17/088,761

(22) Filed: Nov. 4, 2020

(65) Prior Publication Data
US 2021/0303857 A1 Sep. 30, 2021

(30) Foreign Application Priority Data
Mar. 26, 2020 (JP) .............................. JP2020-055888

(51) Int. Cl.
*G06K 9/00* (2022.01)
*G06V 20/20* (2022.01)
(Continued)

(52) U.S. Cl.
CPC ................ *G06V 20/20* (2022.01); *A23L 5/00* (2016.08); *G06K 9/6267* (2013.01); *G06V 20/13* (2022.01); *G06N 20/00* (2019.01)

(58) Field of Classification Search
CPC ......... G06T 2207/30128; G06T 7/0004; G06T 2207/10004; G06T 2207/10028;
(Continued)

(56) References Cited

U.S. PATENT DOCUMENTS

2004/0060986 A1* 4/2004 Bean ...................... G06Q 10/10
235/462.14
2014/0104385 A1* 4/2014 Wong ................... G06Q 30/016
382/110
(Continued)

FOREIGN PATENT DOCUMENTS

JP 2016-180718 10/2016

OTHER PUBLICATIONS

Extended European Search Report for European Patent Application No. 20211361.9 dated May 11, 2021.

*Primary Examiner* — Alex Kok S Liew
(74) *Attorney, Agent, or Firm* — Amin, Turocy & Watson, LLP (57) ABSTRACT

According to an embodiment, an ingredient inquiry system includes a personal-information storing unit, an image input unit, an ingredient discriminating unit, an ingredient specifying unit, and a display. The personal-information storing unit stores, about each of a plurality of individuals, personal information for causing restriction about intake of ingredients used in food and drink. The image input unit inputs an image obtained by photographing the food and drink. The ingredient discriminating unit specifies the food and drink based on the image and discriminates the ingredients used in the food and drink. The ingredient specifying unit collates the personal information corresponding to each of the individuals and the ingredients discriminated by the ingredient discriminating unit and specifies the ingredients corresponding to each of the individuals. The display displays a list of the ingredients corresponding to each of the individuals specified by the ingredient specifying unit.

17 Claims, 7 Drawing Sheets

(51) Int. Cl.
  *A23L 5/00* (2016.01)
  *G06K 9/62* (2022.01)
  *G06V 20/13* (2022.01)
  *G06N 20/00* (2019.01)

(58) Field of Classification Search
  CPC . G06T 2207/10116; G06T 2207/20016; G06T 7/0002; G06T 7/44; G06T 7/593; G06T 7/62; G06T 7/77; G06T 7/80; G06T 1/0007; G06T 1/20; G06T 7/0012; G06V 20/68
  See application file for complete search history.

(56) References Cited

U.S. PATENT DOCUMENTS

| | | |
|---|---|---|
| 2018/0190375 A1 | 7/2018 | Chapela et al. |
| 2019/0295440 A1 | 9/2019 | Hadad |

* cited by examiner

INGREDIENT INQUIRY SYSTEM, INGREDIENT INQUIRY METHOD, AND INGREDIENT INQUIRY PROGRAM

CROSS-REFERENCE TO RELATED APPLICATION

This application is based upon and claims the benefit of priority from Japanese Patent Application No. 2020-055888, filed on Mar. 26, 2020, the entire contents of which are incorporated herein by reference.

FIELD

Embodiments described herein relate generally to an ingredient inquiry system, an ingredient inquiry method, and an ingredient inquiry program.

BACKGROUND

Concerning foods and drinks such as dishes provided in restaurants, in some restaurants, allergy indications or ingredients and the like considered as taboos for religions such as beef and pork are written on menus. However, description targets and standards are different for each of the restaurants. Information that is personally necessary is not always written. We need to ask a store clerk about some information.

Depending on medicines prescribed by doctors and taken, there are ingredients that should not be eaten or drunk such as a grapefruit and caffeine drinks because, for example, the effects of the medicines cannot be obtained. A food and drink providing side cannot deal with such ingredients that should be personally avoided. Foreign visitors speaking different languages can not always communicate with store clerks. It is sometimes difficult to smoothly confirm whether the foreign visitors can take the ingredients used in the food and drink described above.

DETAILED DESCRIPTION

An aspect of embodiments is to provide an ingredient inquiry system, an ingredient inquiry method, and an ingredient inquiry program that make it possible to easily inquire about ingredients used in food and drink for which confirmation is personally necessary.

According to an embodiment, an ingredient inquiry system includes a personal-information storing unit, an image input unit, an ingredient discriminating unit, an ingredient specifying unit, and a display unit. The personal-information storing unit stores, about each of a plurality of individuals, personal information for causing restriction about intake of ingredients used in food and drink. The image input unit inputs an image obtained by photographing the food and drink. The ingredient discriminating unit specifies the food and drink based on the image and discriminates the ingredients used in the food and drink. The ingredient specifying unit collates the personal information corresponding to each of the plurality of individuals and the ingredients discriminated by the ingredient discriminating unit and specifies the ingredients corresponding to each of the plurality of individuals. The display unit displays, as a list, the ingredients corresponding to each of the plurality of individuals specified by the ingredient specifying unit.

An embodiment is explained below with reference to the drawings.

Figure 1:
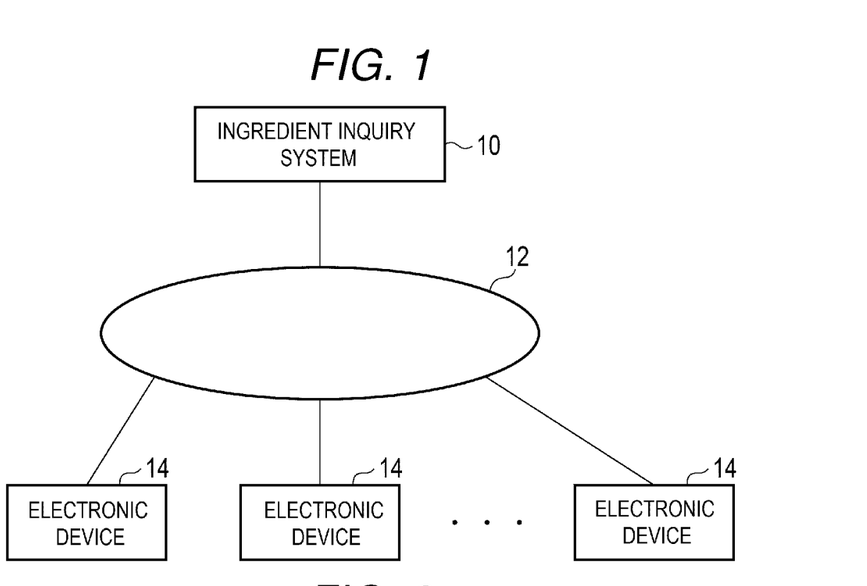
FIG. 1 is an overall configuration diagram of a system according to an embodiment.

FIG. 1 is an overall configuration diagram of a system according to this embodiment. By photographing an image of food and drink such as a dish, the system in this embodiment can inquire about ingredients used in the food and drink. In this embodiment, for example, if personal information for causing restriction about intake of ingredients used in food and drink is set for each of individuals, an inquiry result about a plurality of individuals, for whom different kinds of personal information are respectively set, can be easily acquired by photographing an image of one food or drink. Examples of the restriction about intake of ingredients include allergy ingredients (allergens), medicines being taken, religions, and vegetarian types. Concerning the medicines, there are ingredients that should not be eaten or drunk such as a grapefruit and caffeine drinks because the effects of the medicines cannot be obtained. Concerning the religions, there are ingredients, intake of which is prohibited by doctrines and the like. As the vegetarian types, there are, for example, vegan, dietary vegan, vegetarian, and ovo-lacto vegetarian whose types of restricted ingredients are different. In the personal information, conditions other than the examples described above can be designated.

The system according to this embodiment is configured by an ingredient inquiry system 10 and electronic devices 14 connected via a network 12 such as the Internet.

The ingredient inquiry system 10 in this embodiment provides an ingredient inquiry service for receiving, from the electronic devices 14, images obtained by photographing food and drink and personal information for causing restriction about intake of ingredients used in the food and drink, specifying ingredients corresponding to the personal information (ingredients to be avoided, intake of which should be avoided) included in the food and drink, and causing the electronic devices 14 to display the ingredients.

The ingredient inquiry system 10 may be realized by one computer (server) or may be realized by cloud computing in which a plurality of computers connected via the network 12 cooperate.

The electronic device 14 is an information processing device used by a user who uses a service provided by the ingredient inquiry system 10. The electronic device 14 is realized by, for example, a smartphone, a personal computer, or a tablet computer. The electronic device 14 transmits, to the ingredient inquiry system 10, an image obtained by photographing food and drink such as a dish and personal information of a person who needs confirmation about whether ingredients to be avoided, intake of which should be avoided, are included in ingredients used in the food and drink. The electronic device 14 can inquire the ingredient inquiry system 10 about ingredients targeting a plurality of persons per one dish.

Figure 2:
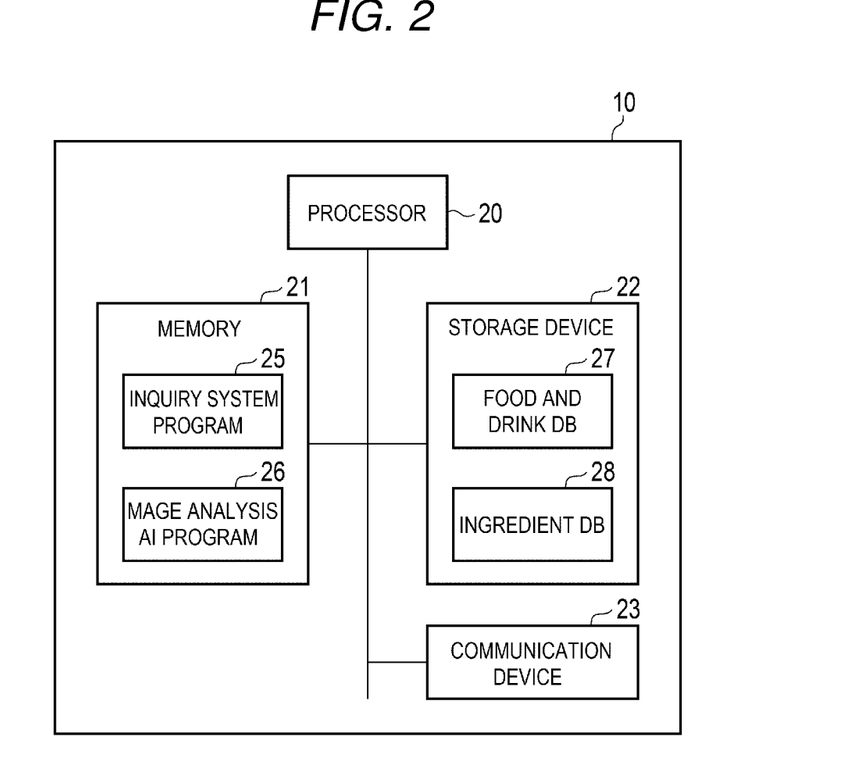
FIG. 2 is a block diagram illustrating a main part circuit configuration of a computer that realizes an ingredient inquiry system.

FIG. 2 is a block diagram illustrating a main part circuit configuration of a computer that realizes the ingredient inquiry system 10. The ingredient inquiry system 10 includes a processor 20, a memory 21, a storage device 22, and a communication device 23.

The processor 20 controls the units according to an operating system or application programs in order to realize various functions of the ingredient inquiry system 10. The processor 20 is, for example, a CPU.

The memory 21 includes a nonvolatile memory region and a volatile memory region. The memory 21 stores the operating system or the application programs in the nonvolatile memory region. The memory 21 sometimes stores, in the nonvolatile or volatile memory regions, data necessary for the processor 20 to execute processing for controlling the units. The memory 21 uses the volatile memory region as a work area where data is rewritten as appropriate by the processor 20. The nonvolatile memory region is, for example, a ROM. The volatile memory region is, for example, a RAM.

The application programs stored in the memory 21 includes, for example, an inquiry system program 25 and an image analysis AI (Artificial Intelligence) program 26. The inquiry system program 25 is a program for collating a plurality of kinds of personal information received from the electronic devices 14 and ingredients (an ingredient list) used in food and drink discriminated by processing of the image analysis AI program 26 and specifying ingredients to be avoided corresponding to each of a plurality of individuals. The image analysis AI program 26 is a program for performing processing for specifying food and drink based on images obtained by photographing food and drink received from the electronic devices 14 and processing for discriminating ingredients used in the specified food and drink. For example, the image analysis AI program 26 specifies food and drink through a visual search for specifying food and drink with an AI technique using a learning model for food and drink recognition prepared in advance.

The storage device 22 is equivalent to an auxiliary storage part of the computer. The storage device 22 is configured by, for example, a HDD or an SSD. The storage device 22 stores, for example, data used by the processor 20 in performing various kinds of processing or data created by processing in the processor 20. The storage device 22 sometimes stores the application programs.

The storage device 22 stores, for example, a food and drink database 27 and an ingredient database 28 used for processing by the inquiry system program 25 and the image analysis AI program 26.

In the food and drink database 27, an ingredient list is registered in which, in association with each of a plurality of foods and drinks specified by the processing by the image analysis AI program 26, ingredients used in the food and drink are registered. In the ingredient database 28, ingredients to be avoided corresponding to each of a plurality of different kinds of personal information are registered.

The communication device 23 controls communication with the electronic devices 14 connected via the network 12.

Figure 3:
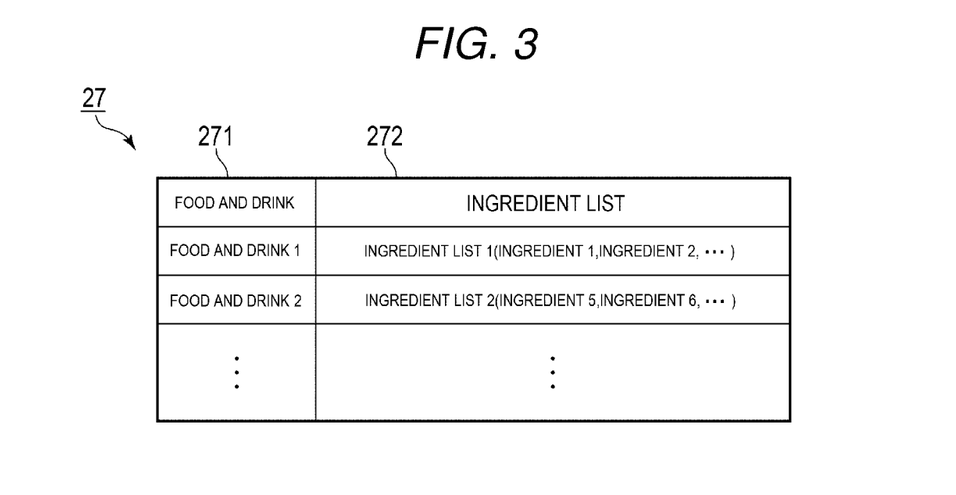
FIG. 3 is a diagram illustrating an example of a data configuration of an ingredient database in the embodiment.

FIG. 3 is a diagram illustrating an example of a data configuration of the food and drink database 27 in this embodiment.

In the food and drink database 27, a plurality of different foods and drinks 271 and ingredient lists 272 corresponding to the respective foods and drinks are registered. The ingredient lists include data indicating a plurality of ingredients used in the food and drink corresponding to the ingredient lists.

Figure 4:
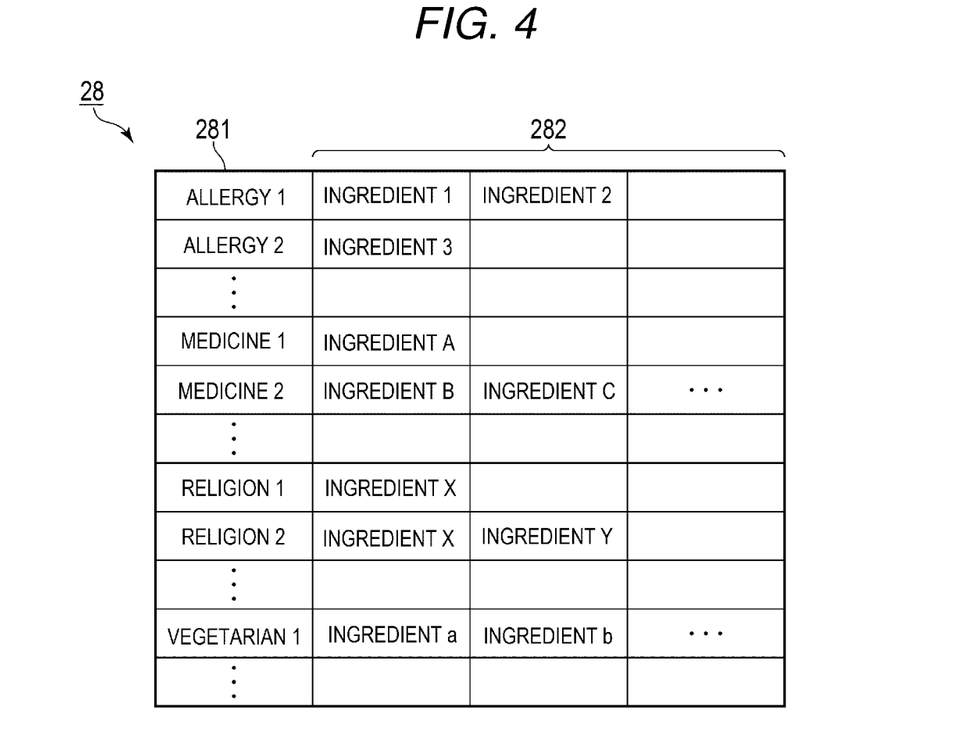
FIG. 4 is a diagram illustrating an example of a data configuration of a food and drink database in the embodiment.

FIG. 4 is a diagram illustrating an example of a data configuration of the ingredient database 28 in this embodiment.

In the ingredient database 28, a plurality of different kinds of personal information 281 designated as inquiry targets from the electronic devices 14 and ingredients (ingredients to be avoided, intake of which should be avoided) 282 corresponding to the respective kinds of personal information are registered in association with each other. For example, "ingredient 3" is registered as the ingredient to be avoided about personal information "allergy 2". As illustrated in FIG. 3, a plurality of ingredients are sometimes registered with respect to one kind of personal information.

Figure 5:
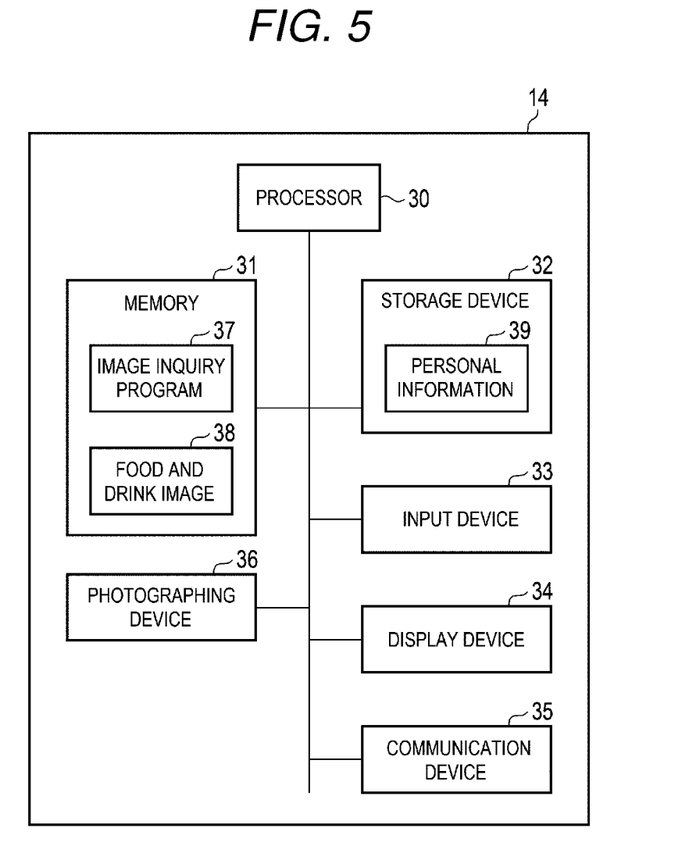
FIG. 5 is a block diagram illustrating a main part circuit configuration of an electronic device.

FIG. 5 is a block diagram illustrating a main part circuit configuration of the electronic device 14. The electronic device 14 includes a processor 30, a memory 31, a storage device 32, an input device 33, a display device 34, a communication device 35, and a photographing device 36.

The processor 30 controls the units according to an operating system or application programs in order to realize various functions of the electronic device 14. The processor 30 is, for example, a CPU.

The memory 31 includes a nonvolatile memory region and a volatile memory region. The memory 31 stores the operating system and the application programs in the nonvolatile memory region. The memory 31 sometimes stores, in the nonvolatile or volatile memory region, data necessary for the processor 30 to execute processing for controlling the units. The memory 31 uses the volatile memory region as a work area where data is rewritten as appropriate by the processor 30. The nonvolatile memory region is, for example, a ROM. The volatile memory region is, for example, a RAM. Programs stored in the memory 31 include an image inquiry program 37 for using an ingredient inquiry service provided by the ingredient inquiry system 10. In the memory 31, for example, a food and drink image 38 obtained by photographing food and drink with the photographing device 36 is stored in order to use the food and drink inquiry service according to the image inquiry program 37.

The storage device 32 is equivalent to an auxiliary storage part of a computer. For example, a HDD or an SDD could be the storage device 32. The storage device 32 saves, for example, data used by the processor 30 in performing various kinds of processing or data created by processing in the processor 30. The storage device 32 sometimes stores the application programs. In the storage device 32, for example, in order to use the ingredient inquiry service, personal information 39 for causing restriction about intake of ingredients used in food and drink is stored about each of a plurality of individuals.

The communication device 35 controls communication with the ingredient inquiry system 10 connected via the network 12.

The input device 33 and the display device 34 are devices that also function as an input device and a display device of the electronic device 14 configured as, for example, a touch panel. The input device 33 detects a touch position on an image displayed by the display device 34 and outputs information concerning the touch position to the processor 30.

The photographing device 36 is used to photograph an image of food and drink in order to use the ingredient inquiry service.

Figure 6:
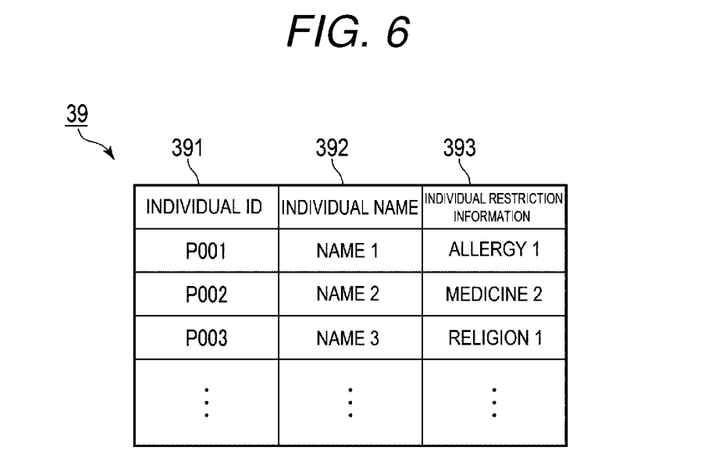
FIG. 6 is a diagram illustrating an example of a data configuration of personal information stored in the electronic device.

FIG. 6 is a diagram illustrating an example of a data configuration of the personal information 39 stored in the electronic device 14.

As illustrated in FIG. 6, in the personal information 39, an individual ID 391, an individual name 392, and individual restriction information 393, which are respectively specific kinds of identification information, are registered in association with a plurality of individuals. The individual restriction information 393 indicates a reason for causing restriction about intake of ingredients used in food and drink. The individual restriction information 393 is equivalent to the personal information 281 registered in the ingredient database 28 of the ingredient inquiry system 10.

The operation of the ingredient inquiry system in this embodiment is explained.

Figure 7:
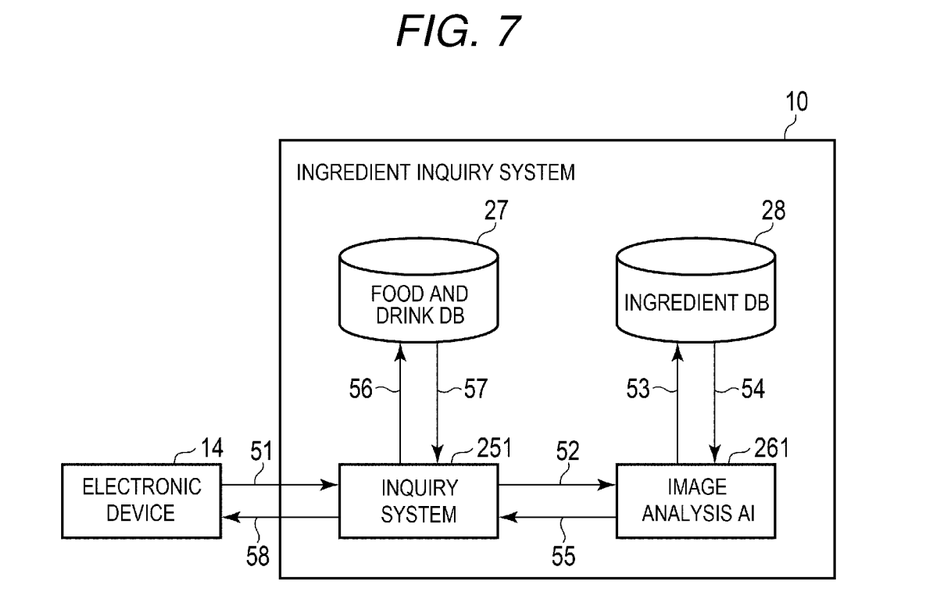
FIG. 7 is a block diagram illustrating a flow of processing of the ingredient inquiry system.

FIG. 7 is a block diagram illustrating a flow of processing of the ingredient inquiry system 10 in this embodiment. In FIG. 7, an inquiry system 251 is a function realized by executing the inquiry system program 25 with the processor 20. An image analysis AI 261 is a function realized by executing the image analysis AI program 26 with the processor 20.

Figure 8:
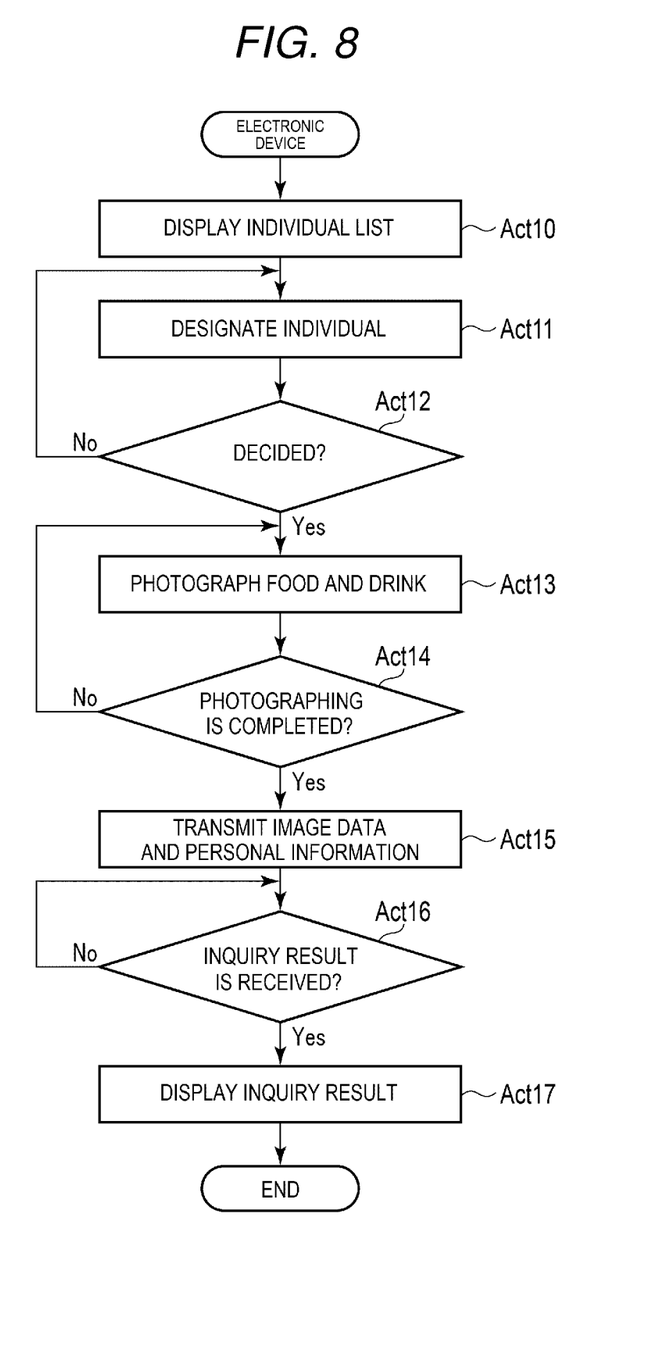
FIG. 8 is a flowchart illustrating processing of the electronic device.
Figure 9:
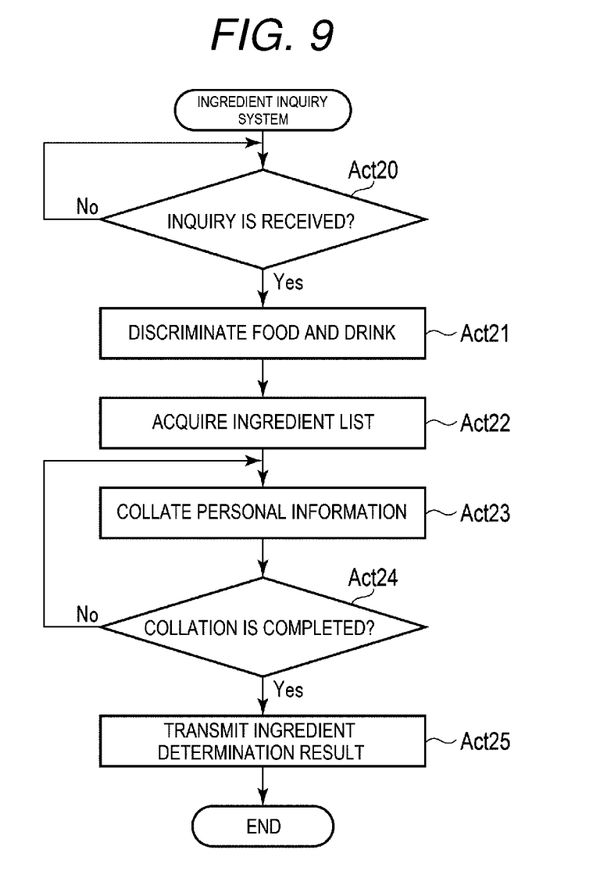
FIG. 9 is a flowchart illustrating processing of the ingredient inquiry system.

FIG. 8 is a flowchart illustrating processing of the electronic device 14 in this embodiment. FIG. 9 is a flowchart illustrating processing of the ingredient inquiry system 10 in this embodiment.

In the electronic device 14, the image inquiry program 37 is installed in order to use the ingredient inquiry service provided by the ingredient inquiry system 10. Before the ingredient inquiry service is used, registration processing for the personal information 39 is executed by the function of the image inquiry program 37.

For example, in the registration processing for the personal information 39, an individual name is input and individual restriction information, which is a reason for causing restriction about intake of ingredient used in food and drink, is set. Examples of the reason for causing restriction about intake of ingredient include medicines being taken, religions, allergens, and vegetarian types. The electronic device 14 sets a specific individual ID for a pair of the individual name and the individual restriction information and stores the individual ID as the personal information 39.

If the electronic device 14 is used in a nursery school or the like, personal information about a plurality of nursery school children is registered in advance. Consequently, it is possible to inquire the ingredient inquiry system 10 collectively about the plurality of nursery school children whether ingredients that the nursery school children cannot eat (that should be paid attention) are included in one dish.

If execution of the image inquiry program 37 is instructed by operation from the input device 33, the processor 30 of the electronic device 14 causes, based on the personal information 39 registered in advance, the display device 34 to display an individual list for selecting an individual to be set as an inquiry target (Act 10 in FIG. 8).

Figure 10:
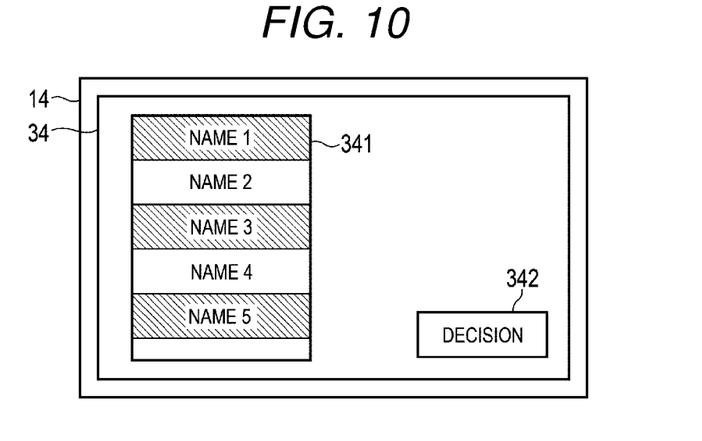
FIG. 10 is a diagram illustrating an example of an individual list screen displayed on a display device of the electronic device.

FIG. 10 is a diagram illustrating an example of an individual list screen displayed on the display device 34 of the electronic device 14. A list display area 341 in which a plurality of individual names registered in advance are displayed and a decision button 342 are provided on the individual list screen.

The displayed individual names can be changed by scrolling the list display area 341 with slide operation or the like on the input device 33 by the user. In the list display area 341, an individual name can be optionally displayed in a selected state by touch operation on the input device 33 by the user.

If detecting that touch operation is performed in the list display area 341, the processor 30 causes the display device 34 to display an individual name in the selected state (Act 11). A plurality of individual names can be displayed in the selected state (No in Act 12). In FIG. 10, "name 1", "name 3", and "name 5" are displayed in the selected state by being designated by user operation.

If the selection of the individual names is instructed by user operation on the decision button 342 (Yes in Act 12), the processor 30 reads out, from the personal information 39, individual IDs and individual control information corresponding to the individual names selected in the list display area 341 and causes the memory 31 to store the individual IDs and the individual control information as collation target data.

If the selection of the individual names is decided, the processor 30 starts the photographing device 36 and shifts to a photographing mode for photographing an image of food and drink set as an inquiry target. If the image of the food and drink is photographed by user operation using an image photographing function provided in the electronic device 14, the processor 30 causes the memory 31 to store the photographed food and drink image 38. The processor 30 causes the display device 34 to display the photographed food and drink image 38. If the food and drink image 38 intended by the user is not successfully photographed (Yes in Act 14), an image of the food and drink can be repeatedly photographed.

Figure 11:
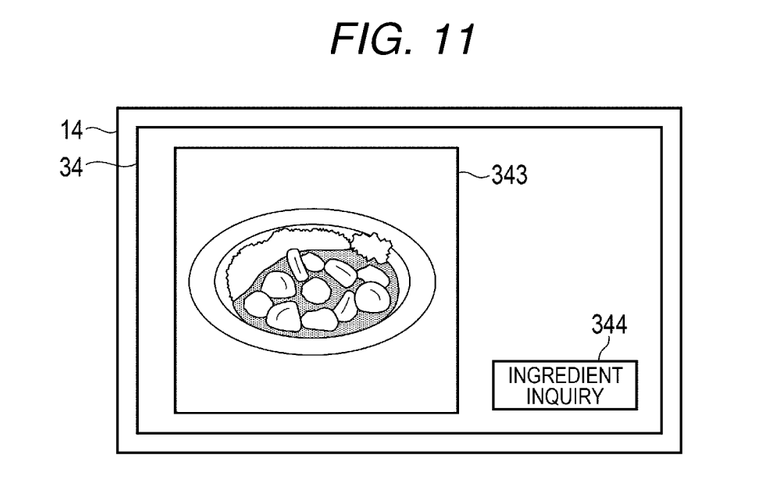
FIG. 11 is a diagram illustrating an example of a food and drink image display screen displayed on the display device.

FIG. 11 is a diagram illustrating an example of a food and drink image display screen displayed on the display device 34 of the electronic device 14. An image display area 343 in which a photographed food and drink image is displayed and an ingredient inquiry button 344 are provided on the food and drink image display screen.

If ingredient image photographing completion and inquiry execution are instructed by user operation on the ingredient inquiry button 344 (Yes in Act 14), the processor 30 transmits an inquiry request to the ingredient inquiry system 10 together with the food and drink image 38 set as an inquiry target and data of personal information (an individual ID and individual restriction information) (Act 15) (51 in FIG. 7).

If receiving the inquiry request from the electronic device 14 through the communication device 23 (Yes in Act 20 in FIG. 9), the processor 20 of the ingredient inquiry system 10 provides data of a food and drink image from the inquiry system 251 to the image analysis AI 261 and requests specifying of food and drink requested as a collation target (52 in FIG. 7).

The image analysis AI 261 specifies food and drink based on the data of the food and drink image through a visual search for specifying food and drink with an AI technique (Act 21). The image analysis AI 261 searches through the food and drink database 27 based on the specified food and drink (53 in FIG. 7) and acquires an ingredient list corresponding to the food and drink from the food and drink database 27 (Act 22) (54 in FIG. 7). The image analysis AI 261 provides the ingredient list acquired from the ingredient database 28 to the inquiry system 251 (55 in FIG. 7).

The inquiry system 251 collates the ingredient list acquired from the image analysis AI 261 and an ingredient discriminated based on the ingredient database 28 according to the individual restriction information received from the electronic device 14 (Act 23). Consequently, the inquiry system 251 discriminates whether ingredients to be avoided, intake of which should be avoided, corresponding to the individual restriction information are included in the food and drink specified based on the food and drink image.

That is, the inquiry system 251 retrieves the personal information 281 of the ingredient database 28 based on individual restriction information for one person (corresponding to one individual ID) (56 in FIG. 7). For example, the inquiry system 251 retrieves "allergy 1" from the personal information 281 based on individual restriction information "allergy 1". The inquiry system 251 acquires the ingredients 282 registered to correspond to the personal information retrieved from the personal information 281 (57 in FIG. 7). For example, "ingredient 1" and "ingredient 2" can be acquired as ingredients to be avoided for "allergy 1" of the personal information 281.

The inquiry system 251 discriminates whether the ingredients to be avoided corresponding to the individual restriction information acquired from the ingredient database are included in the ingredient list acquired from the image analysis AI 261. If the ingredients to be avoided are included in the ingredient list, the inquiry system 251 stores the relevant ingredients (the ingredients to be avoided) in association with an individual ID corresponding to the individual restriction information set as the processing target.

If receiving individual restriction information of a plurality of individuals (individual IDs) from the electronic device 14, in the same manner as explained above, about all kinds of individual restriction information, the inquiry system 251 discriminates whether ingredients corresponding to individual restriction information for each of the individuals are included in the ingredient list (food and drink) (Acts 23 and 24).

If completing the collation about all the kinds of individual restriction information (Yes in Act 24), the inquiry system 251 transmits an ingredient determination result (an inquiry result) for each of the individuals determined by the collation to the electronic device 14 and causes the electronic device 14 to display the ingredient determination result (the inquiry result) (Act 25) (58 in FIG. 7). That is, the inquiry system 251 transmits, to the electronic device 14, as an inquiry result, a name of the food and drink specified by the image analysis AI 261 based on the image and data of ingredients to be avoided corresponding to each of a plurality of individual IDs.

If receiving the inquiry result from the ingredient inquiry system 10 (Yes in Act 16 in FIG. 8), the processor 30 of the electronic device 14 causes the display device 34 to display the inquiry result.

Figure 12:
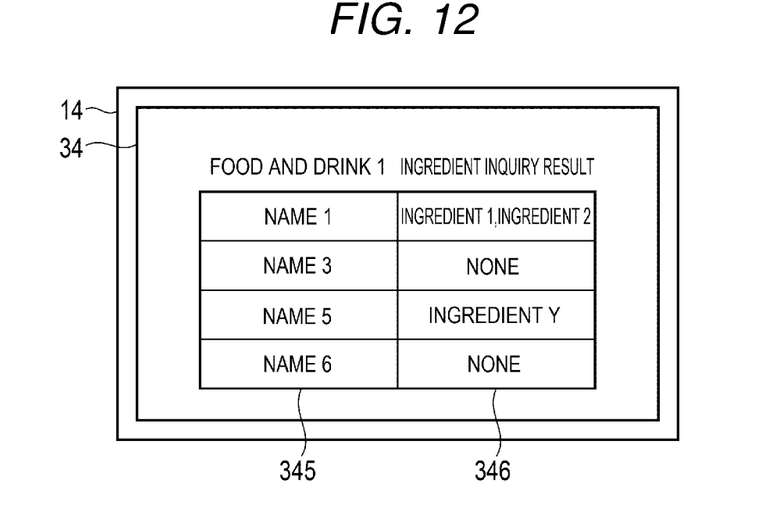
FIG. 12 is a diagram illustrating an example of an inquiry result display screen displayed on the display device.

FIG. 12 is a diagram illustrating an example of an inquiry result display screen displayed on the display device 34 of the electronic device 14. The processor 30 causes, based on data indicating the inquiry result received from the ingredient inquiry system 10, the display device 34 to display a name "food and drink 1" of the food and drink specified based on the food and drink image 38 and a list of inquiry results. In the list of inquiry results, individual names 345 of individuals selected as an inquiry target in the list display area 341 and ingredients to be avoided 346 set as an ingredient inquiry result are displayed in association with each other.

That is, the processor 30 discriminates an individual name based on the individual ID included in the inquiry result and causes the display device 34 to display ingredients associated with the individual name. For example, in the example illustrated in FIG. 12, it is indicated that "ingredient 1" and "ingredient 2", which are ingredients to be avoided that an individual "name 1" should avoid taking, are included in food and drink "food and drink 1". It is indicated that an ingredient to be avoided that an individual "name 3" should avoid taking is not included in the food and drink "food and drink 1".

In this way, the electronic device 14 photographs an image of food and drink set as an inquiry target, selects an individual who needs confirmation, and transmits an inquiry request to the ingredient inquiry system 10. Consequently, it is possible to easily confirm whether ingredients to be avoided, intake of which should be avoided for individuals, are included in food and drink set as a target. That is, simply by photographing food and drink, it is possible to easily inquire whether ingredients, which are allergens, are not included in the food and drink, whether adversely affecting medicines are not included in medicines being taken, and whether ingredients considered taboos for religions are absent. It is unnecessary to designate all ingredients to be avoided themselves for each of individuals in the inquiry. Restricting contents for intake of ingredients (for example, allergy ingredients (allergens), medicines being taken, religions, and vegetarian types) only have to be designated. Therefore, it is easy to confirm ingredients with individuals with whom it is difficult to communicate such as foreign visitors.

The several embodiments are explained above. However, the embodiments are presented as examples and are not intended to limit the scope of the invention. These new embodiments can be implemented in other various forms. Various omissions, substitutions, and changes can be made without departing from the spirit of the invention. These embodiments and modifications of the embodiments are included in the scope and the gist of the invention and included in the inventions described in claims and the scope of equivalents of the inventions.

The processing described in the embodiment can be provided to various devices while being written in a recording medium such as a magnetic disk (a flexible disk, a hard disk, or the like), an optical disk (a CD-ROM, a DVD, or the like), or a semiconductor memory as a computer-executable program. The processing can also be transmitted by a communication medium and provided to the various devices. The computer reads the program recorded in the recording medium or receives the program via the communication medium and executes the processing by the operation of the computer being controlled by the program.

What is claimed is:
1. An ingredient inquiry system, comprising:
a processor configured to:
store, about each of a plurality of individuals, personal information for causing restriction about intake of ingredients used in food and drink;

input an image representing the food and drink;
specify the food and drink based on the image and discriminate the ingredients used in the food and drink;
collate the personal information corresponding to each of the plurality of individuals and the ingredients as used in the food and drink and specify the ingredients corresponding to each of the plurality of individuals;
display a list the ingredients corresponding to each of the plurality of individuals;
select an individual set as a collation target out of the plurality of individuals whose personal information is stored, and
specify ingredients based on the personal information corresponding to the individual selected.

2. The ingredient inquiry system according to claim 1, wherein the personal information includes information indicating medicines, religions, allergens, and vegetarian types corresponding to the individuals.

3. The ingredient inquiry system according to claim 1, wherein the image representing the food and drink is obtained by photographing the food and drink.

4. The ingredient inquiry system according to claim 1, wherein the image is input using a smartphone.

5. The ingredient inquiry system according to claim 1, wherein the processor is further configured to specify the food and drink based on the image and discriminate generic categories of the ingredients used in the food and drink.

6. The ingredient inquiry system according to claim 1, wherein the processor is further configured to specify the food and drink based on the image and discriminate individual components of ingredients used in the food and drink.

7. An ingredient inquiry system, comprising:
a processor configured to:
receive, from an electronic device, for a plurality of individuals, personal information for causing restriction about intake of ingredients used in food and drink;
receive an image representing the food and drink from the electronic device;
specify the food and drink based on the image and discriminate the ingredients used in the food and drink;
collate the personal information corresponding to each of the plurality of individuals and the ingredients as used in the food and drink and specify the ingredients corresponding to each of the plurality of individuals; and
list the ingredients corresponding to each the plurality of individuals;
select an individual set as a collation target out of the plurality of individuals whose personal information is stored by the personal-information storing component, and
specify ingredients based on the personal information corresponding to the individual selected.

8. The ingredient inquiry system according to claim 7, wherein the personal information includes information indicating medicines, religions, allergens, and vegetarian types corresponding to the individuals.

9. The ingredient inquiry system according to claim 7, wherein the image representing the food and drink is obtained by photographing the food and drink.

10. The ingredient inquiry system according to claim 7, wherein the personal information for causing the restriction about the intake of ingredients used in the food and drink is received from a server.

11. The ingredient inquiry system according to claim 7, wherein the processor is further configured to specify the food and drink based on the image and discriminate generic categories of the ingredients used in the food and drink.

12. The ingredient inquiry system according to claim 7, wherein the processor is further configured to specify the food and drink based on the image and discriminate individual components of ingredients used in the food and drink.

13. An ingredient inquiry method, comprising:
storing, about each of a plurality of individuals, personal information for causing restriction about intake of ingredients used in food and drink;
inputting an image representing the food and drink;
specifying the food and drink based on the image and discriminating the ingredients used in the food and drink;
collating the personal information corresponding to each of the plurality of individuals and the discriminated ingredients and specifying the ingredients corresponding to each of the plurality of individuals;
displaying, as a list, the ingredients corresponding to each of the specified plurality of individuals;
selecting an individual set as a collation target out of the plurality of individuals whose personal information is stored; and
specifying ingredients based on the personal information corresponding to the individual selected.

14. The ingredient inquiry method according to claim 13, wherein the personal information includes information indicating medicines, religions, allergens, and vegetarian types corresponding to the individuals.

15. The ingredient inquiry method according to claim 13, wherein the image representing the food and drink is obtained by photographing the food and drink.

16. The ingredient inquiry method according to claim 13, further comprising:
specifying the food and drink based on the image and discriminate generic categories of the ingredients used in the food and drink.

17. The ingredient inquiry method according to claim 13, further comprising:
specifying the food and drink based on the image and discriminate individual components of ingredients used in the food and drink.

* * * * *